US007803530B2

(12) United States Patent
Cohenford et al.

(10) Patent No.: US 7,803,530 B2
(45) Date of Patent: Sep. 28, 2010

(54) DETECTION AND TYPING OF HUMAN PAPILLOMAVIRUS USING PNA PROBES

(75) Inventors: Menashi A. Cohenford, West Warwick, RI (US); Brian Lentrichia, Acton, MA (US)

(73) Assignee: Cytyc Corporation, Marlborough, MA (US)

( * ) Notice: Subject to any disclaimer, the term of this patent is extended or adjusted under 35 U.S.C. 154(b) by 1769 days.

(21) Appl. No.: 10/323,188

(22) Filed: Dec. 18, 2002

(65) Prior Publication Data
US 2003/0108866 A1 Jun. 12, 2003

Related U.S. Application Data

(62) Division of application No. 09/825,482, filed on Apr. 3, 2001, now abandoned.

(60) Provisional application No. 60/194,304, filed on Apr. 3, 2000, provisional application No. 60/225,524, filed on Aug. 15, 2000.

(51) Int. Cl.
*C12Q 1/68* (2006.01)
*C07H 21/04* (2006.01)
(52) U.S. Cl. .................. 435/6; 536/24.31; 536/24.32
(58) Field of Classification Search .................. 435/6, 435/91.2; 536/24.31, 24.32
See application file for complete search history.

(56) References Cited

U.S. PATENT DOCUMENTS

| 4,849,332 | A | * | 7/1989 | Lorincz .................. 435/5 |
| 4,908,306 | A | | 3/1990 | Lorincz |
| 4,983,728 | A | | 1/1991 | Herzog et al. |
| 5,143,627 | A | | 9/1992 | Lapidus et al. |
| 5,182,377 | A | | 1/1993 | Manos et al. |
| 5,256,571 | A | | 10/1993 | Hurley et al. |
| 5,283,171 | A | | 2/1994 | Manos et al. |
| 5,364,758 | A | | 11/1994 | Meijer et al. |
| 5,411,857 | A | | 5/1995 | Beaudenon et al. |
| 5,447,839 | A | | 9/1995 | Manos et al. |
| 5,484,699 | A | | 1/1996 | Bouma et al. |
| 5,527,898 | A | | 6/1996 | Bauer et al. |
| 5,539,082 | A | | 7/1996 | Nielsen et al. |
| 5,543,294 | A | | 8/1996 | Silverstein et al. |
| 5,580,970 | A | | 12/1996 | Hendricks et al. |
| 5,629,178 | A | | 5/1997 | Demers |
| 5,639,871 | A | * | 6/1997 | Bauer et al. .................. 536/24.3 |
| 5,643,715 | A | | 7/1997 | Lancaster |
| 5,648,459 | A | | 7/1997 | Cole et al. |
| 5,656,461 | A | | 8/1997 | Demers |
| 5,679,509 | A | | 10/1997 | Wheeler et al. |
| 5,705,627 | A | | 1/1998 | Manos et al. |
| 5,712,092 | A | | 1/1998 | Orth et al. |
| 5,719,028 | A | | 2/1998 | Dahlberg et al. |
| 5,731,416 | A | | 3/1998 | Garner |
| 5,750,334 | A | | 5/1998 | Cerutti et al. |
| 5,783,412 | A | | 7/1998 | Morris et al. |
| 5,837,466 | A | | 11/1998 | Lane et al. |
| 5,846,729 | A | | 12/1998 | Wu et al. |
| 5,849,497 | A | * | 12/1998 | Steinman .................. 435/6 |
| 5,854,033 | A | | 12/1998 | Lizardi |
| 5,863,717 | A | * | 1/1999 | Lancaster et al. .................. 435/5 |
| 5,874,213 | A | | 2/1999 | Cummins et al. |
| 5,876,922 | A | | 3/1999 | Orth et al. |
| 5,888,724 | A | | 3/1999 | Silverstein et al. |
| 5,888,733 | A | | 3/1999 | Hyldig-Nielsen et al. |
| 5,891,625 | A | | 4/1999 | Buchardt et al. |
| 5,942,391 | A | | 8/1999 | Zhang et al. |
| 5,958,674 | A | | 9/1999 | Beaudenon et al. |
| 5,958,738 | A | | 9/1999 | Lindemann et al. |
| 5,981,173 | A | | 11/1999 | Orth et al. |
| 5,985,563 | A | | 11/1999 | Hyldig-Nielsen et al. |
| 6,020,124 | A | | 2/2000 | Sorenson |
| 6,037,130 | A | | 3/2000 | Tyagi et al. |
| 6,045,993 | A | * | 4/2000 | Mahony et al. .................. 435/5 |
| 6,110,676 | A | | 8/2000 | Coull et al. |
| 6,169,169 | B1 | * | 1/2001 | Hyldig-Nielsen et al. .. 536/22.1 |
| 6,218,104 | B1 | | 4/2001 | Morris et al. |
| 6,509,149 | B2 | | 1/2003 | Roberts et al. |
| 6,969,585 | B2 | * | 11/2005 | Lorincz et al. .................. 435/6 |

FOREIGN PATENT DOCUMENTS

| WO | WO 92/20702 | 11/1992 |
| WO | WO 95/13399 | 5/1995 |
| WO | WO 97/39008 | 10/1997 |
| WO | WO 9817829 A2 * | 4/1998 |

OTHER PUBLICATIONS

Behn M. et al., "Simple and Reliable Factor V Genotyping by PNA-Mediated PCR Clamping" *Thromb Haemost.* vol. 79, 1998, pp. 773-777.

Cochet O. et al., "Selective PCR Amplification of Functional Immunoglobulin Light Chain from Hybridoma Containing the Aberrant MOPC 21-Derived Vκ by PNA-Mediated PCR Clamping" *Biotechniques*, vol. 26, No. 5, 1999, 818-822.

"Detection of E6 Gene Region DNA of High-Risk Human Papillomavirus Types Using E6 Gene Region Primers" *Biosearch International*, Aug. 2000, pp. 1-22.

Demers D. B. et al., "Enhanced PCR Amplification of VNTR Locus D1S80 Using Peptide Nucleic Acid (PNA)" *Nucleic Acids Research*, vol. 23. No. 15. 1995, pp. 3050-3055.

Hansen M. H. et. al., " Detection of PNA/DNA Hybrid Molecules by Antibody Fab Fragments Isolated from a Phage Display Library" *Journal of Immunological Methods*, vol. 203, No. 2, 1997, pp. 199-207.

Kyger E. M. et al., "Detection of the Hereditary Hemochromatosis Gene Mutation by Real-Time Fluorescence Polymerase Chain Reaction and Peptide Nucleic Acid Clamping" *Analytical Biochemistry*, vol. 260, No. 2, 1998, pp. 142-148.

(Continued)

*Primary Examiner*—Suryaprabha Chunduru
(74) *Attorney, Agent, or Firm*—Theodore Allen

(57) ABSTRACT

The invention provides methods for detection and typing of HPV infection using PNA probes. More specifically, methods are provided for detecting high-risk types of HPV infection with minimal numbers of PNA probes or using PNA probes to selectively amplify only high-risk types of HPV.

18 Claims, 4 Drawing Sheets

OTHER PUBLICATIONS

Mrozikicwicz O.M. et al., "Peptide Nucleic Acid-Mediated Polymerase Chain Reaction Clamping Allows Allelic Allocation of CYP1A1 Mutations" *Analytical Biochemistry*, vol. 250, No. 2. 1997, pp. 256-257.

Orum H. et al., "Single Base Pair Mutation Analysis by PNA Directed PCT Clamping" *Nucleic Acids Research*, Vo. 21, No. 23, 1993, pp. 5332-5336.

Sano T. et al.. "In Situ Hybridization with Biotinylated Tryamide Amplification: Detection of Human Papillomavirus DNA in Cervical Neoplastic Lesions" *Modern Pathology*, vol. 11. No. 1. 1998, pp. 19-23.

Seeger et al., "PNA-Mediated Purification of PCR Amplifiable Human Genomic DNA from Whole Blood" *BioTechniones*, vol. 23. No. 3. 1997. pp. 512-517.

Uhlmann E., "Peptide Nucleic Acids (PNA) and PNA-DNA Chimeras: From High Binding Affinity Towards Biological Function" *Biol. Chemistry*, 1998, 379 (8-9) pp. 1044-1052.

von Wintzingerods F. et al., "Peptide Nucleic Acid-Mediated PCR Clamping as a Useful Supplement in the Determination of Microbial Diversity" *Applied and Environmental Microbiology*, vol. 66, No. 2, Feb. 2000, pp. 549-557.

Zhong S. et al., "Detection of Apoliporotein B mRNA Editing by Peptide Nucleic Acid Mediated PCR Clamping" *Biochemical and Biophysical Research Communication*, vol. 259, No. 2, 1999, pp. 311-313.

\* cited by examiner

Competitive inhibition of DNA amplification by a blocking probe

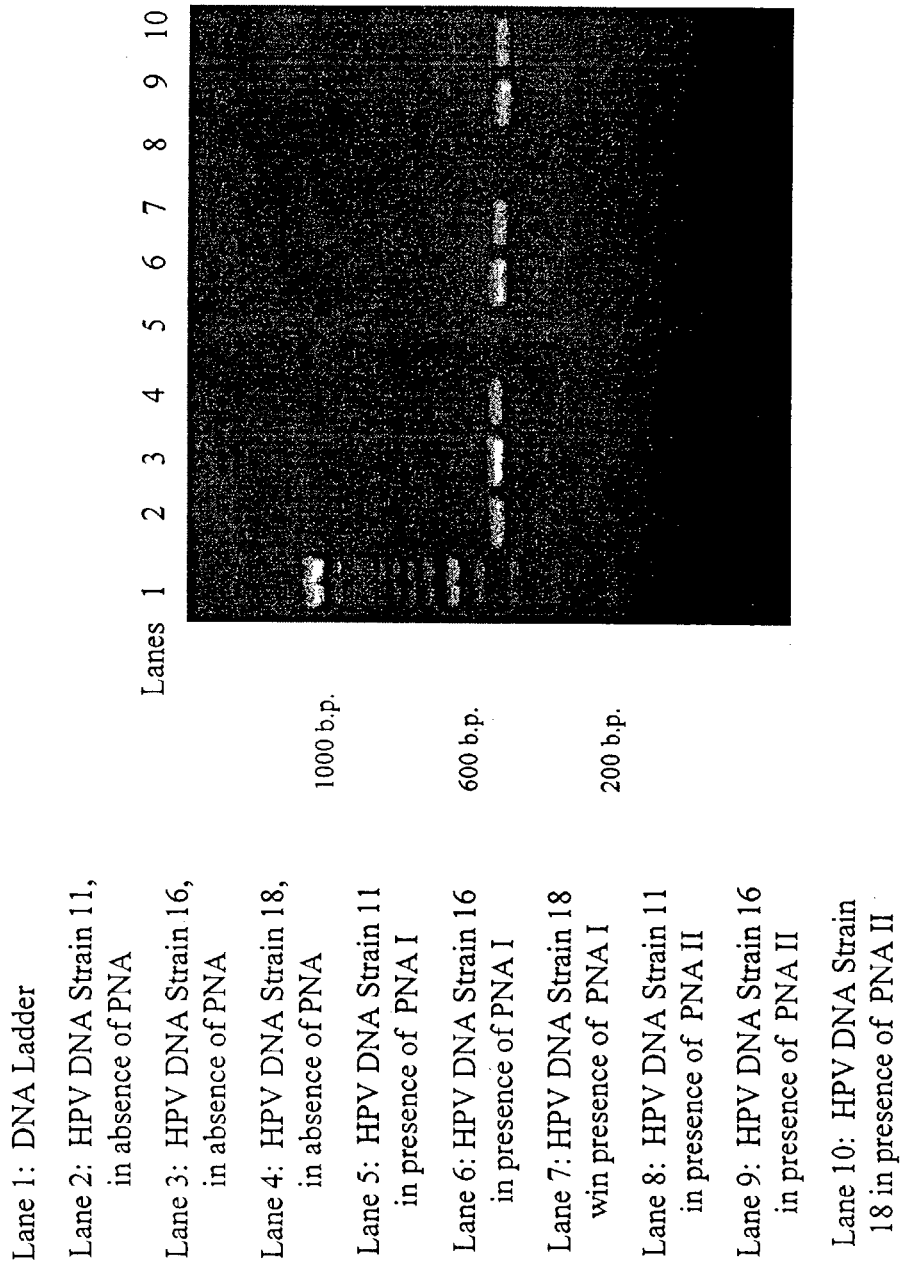

Lane 1: DNA Ladder

Lane 2: HPV DNA Strain 11, in absence of PNA

Lane 3: HPV DNA Strain 16, in absence of PNA

Lane 4: HPV DNA Strain 18, in absence of PNA

Lane 5: HPV DNA Strain 11 in presence of PNA I

Lane 6: HPV DNA Strain 16 in presence of PNA I

Lane 7: HPV DNA Strain 18 win presence of PNA I

Lane 8: HPV DNA Strain 11 in presence of PNA II

Lane 9: HPV DNA Strain 16 in presence of PNA II

Lane 10: HPV DNA Strain 18 in presence of PNA II

Figure 3  Selective PCR amplification of HPV DNA using PNA blocking probes

Effect of PNA concentration on HPV DNA (STRAIN 18) PCR

Lanes

Lane 1- DNA negative control

Lane 2- HPV DNA Strain 18 in presence of 1uM PNA III

Lane 3- HPV DNA Strain 18 in presence of 10uM PNA III

Lane 4- HPV DNA Strain 18 in absence of PNA III

Lane 5- DNA ladder

```
                              SEQUENCE LISTING

<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: PNA Probe I

<400> SEQUENCE: 1
actgttgttg atact                                                        15

<210> SEQ ID NO 2
<211> LENGTH: 14
<212> TYPE: DNA
<213> ORGANISM: Artificial Sequence
<220> FEATURE:
<223> OTHER INFORMATION: PNA Probe II

<400> SEQUENCE: 2
agataccact ccca                                                         14

<210> SEQ ID NO 3
<211> LENGTH: 14
<212> TYPE: DNA
<213> ORGANISM: Artificial Sequence
<220> FEATURE:
<223> OTHER INFORMATION: PNA Probe III

<400> SEQUENCE: 3
gataccactc gcag                                                         14

<210> SEQ ID NO 4
<211> LENGTH: 14
<212> TYPE: DNA
<213> ORGANISM: Artificial Sequence
<220> FEATURE:
<223> OTHER INFORMATION: PNA Probe IV

<400> SEQUENCE: 4
ccttacacca ccgc                                                         14

<210> SEQ ID NO 5
<211> LENGTH: 14
<212> TYPE: DNA
<213> ORGANISM: Artificial Sequence
<220> FEATURE:
<223> OTHER INFORMATION: PNA Probe V

<400> SEQUENCE: 5
gacactaccc gcag                                                         14

<210> SEQ ID NO 6
<211> LENGTH: 15
<212> TYPE: DNA
<213> ORGANISM: Artificial Sequence
<220> FEATURE:
<223> OTHER INFORMATION: PNA Probe VI

<400> SEQUENCE: 6
agataccaca cgcag                                                        15
```

```
<210> SEQ ID NO 7
<211> LENGTH: 17
<212> TYPE: DNA
<213> ORGANISM: Artificial Sequence
<220> FEATURE:
<223> OTHER INFORMATION: PNA Probe VII

<400> SEQUENCE: 7
tagataccac acgcagt                                                    17

<210> SEQ ID NO 8
<211> LENGTH: 15
<212> TYPE: DNA
<213> ORGANISM: Artificial Sequence
<220> FEATURE:
<223> OTHER INFORMATION: PNA Probe VIII

<400> SEQUENCE: 8
agataccact cccag                                                      15

<210> SEQ ID NO 9
<211> LENGTH: 22
<212> TYPE: DNA
<213> ORGANISM: Artificial Sequence
<220> FEATURE:
<223> OTHER INFORMATION: MC01 HPV consensus primer sequence

<400> SEQUENCE: 9
tgaggaagat accacacgca gt                                              22

<210> SEQ ID NO 10
<211> LENGTH: 20
<212> TYPE: DNA
<213> ORGANISM: Artificial Sequence
<220> FEATURE:
<223> OTHER INFORMATION: MY09 consensus primer

<400> SEQUENCE: 10
cgtccmarrg gawactgatc                                                 20

<210> SEQ ID NO 11
<211> LENGTH: 20
<212> TYPE: DNA
<213> ORGANISM: Artificial Sequence
<220> FEATURE:
<223> OTHER INFORMATION: MY11 consensus primer

<400> SEQUENCE: 11
gcmcagggwc ataayaatgg                                                 20
```

DETECTION AND TYPING OF HUMAN PAPILLOMAVIRUS USING PNA PROBES

CROSS-REFERENCE TO RELATED APPLICATIONS

This application is a divisional application of U.S. patent application Ser. No. 09/825,482 filed on Apr. 3, 2001, now abandoned, which claims benefit and priority from each of the following provisional applications under 37 CFR §1.78: U.S. Provisional Application Ser. No. 60/194,304 filed Apr. 3, 2000, and U.S. Provisional Application Ser. No. 60/225,524 filed Aug. 15, 2000 all of which are incorporated herein by reference in their entirety.

GOVERNMENT RIGHTS

Work described herein was supported by SBIR Grant No. 1R43CA80401-01, awarded by the National Cancer Institute. The Government has certain rights in the invention.

BACKGROUND OF THE INVENTION

Epidemiological studies have long implicated the human papillomavirus (HPV) as a major cause of cervical neoplasia and cancer. Nonetheless, it has been only within the last decade that a vast body of evidence has been generated to support a causal role of HPV in the etiology of cervical neoplasia and cancer. More than 70 types of HPV have been identified. However, not all HPV types are implicated in cervical cancer. Several types have been associated with a high risk for cervical disease, including types 16, 18, 31, 33, 35, 39, 45, 51, 53, 52, 56, 58, 59, 66, 68, and 70. The detection of these high-risk types of HPV is important in the accurate and timely diagnosis of HPV-related diseases.

Consequently, a variety of methods for detecting high-risk types of HPV have been devised. Many of those rely on the detection of unique sequences in the HPV genome. For example, DNA or RNA probes complementary to a portion of the genes of a particular high risk HPV strain have been reported in U.S. Pat. No. 4,849,332 to Lorincz, incorporated herein by reference, as useful in screening for the presence of a particular strain of high-risk HPV in patient samples. U.S. Pat. No. 5,705,627 to Manos et al., incorporated herein by reference, reports use of polymerase chain reaction (PCR) to amplify and detect HPV DNA using degenerate or mixed consensus primers, followed by typing using a mixture of genotype-specific DNA probes. PCR amplification provides a more sensitive method of detecting HPV DNA, but because existing PCR consensus primers hybridize to both high-risk types of HPV and low-risk types, the need for subsequent typing still exists. Using a cocktail of probes specific for various high-risk genotypes, on the other hand, is costly, time-consuming and requires large quantities of reagents and sample DNA. Therefore, there exists the need for a more economical method of detecting all the high-risk HPV types that are of concern.

SUMMARY OF THE INVENTION

Methods of the invention comprise detecting and/or typing variants of a disease organism. In a preferred embodiment, methods are used to detect nucleic acids associated with HPV, which in turn provides a basis for medical diagnosis and treatment. Methods of the invention solve the problems in the art through two approaches: the first approach minimizes the amount of probes needed for screening for all the variants of concern, e.g., all the high-risk strains of a disease organism. The second approach limits the strains amplified by an amplification-based (e.g. PCR-based) detection method.

In one aspect of the invention, methods are provided for detecting the presence of specific HPV target nucleic acids in biological samples using peptide-nucleic acid (PNA) probes. Preferred methods comprise suspending sample cells in a solution; isolating one or more HPV target nucleic acids from the sample cells; contacting the target nucleic acids with at least one PNA probe that is substantially complementary to at least a portion of a nucleic acid, the detection of which is desired; and detecting hybridization between the PNA probe and a target nucleic acid. Preferably, the solution for suspending the sample cells contains an alcohol in an amount sufficient to fix sample cells without coagulation, an anti-clumping agent, and a buffer that maintains the solution at a pH within a range of about 4 to 7.

In a preferred embodiment, the presence of the target nucleic acid in the sample cells is diagnostic of HPV infection, and may be indicative of risks of cancer, such as risks associated with endocervical carcinoma, cervical cancer, and neoplasia.

In another embodiment, the presence of the target nucleic acid sequence is indicative of the presence of a particular type of HPV. In more preferred embodiments, the target nucleic acid sequence is indicative of the presence of HPV strains selected from types 16, 18, 31, 33, 35, 39, 45, 51, 52, 56, 58, 59, 68 and 70.

In other preferred embodiments, methods of the invention further comprise capturing the target nucleic acid onto a solid support using PNA-DNA interaction.

Alternative embodiments of the invention include methods for detecting the presence of a target nucleic acid of a HPV in a sample, comprising: capturing candidate nucleic acids onto a solid support with at least one PNA probe that is substantially complementary to at least a portion of nucleic acids of one or more HPV types and then detecting hybridization between the PNA probe and a target nucleic acid. Other embodiments relate to methods for in situ detection of a target nucleic acid of a HPV in a sample by transferring suspended sample cells uniformly onto a surface; in situ hybridizing a target nucleic acid of a HPV contained in the cells with at least one PNA probe that is substantially complementary to portions of nucleic acids of one or more HPV types; and detecting hybridization between the PNA probe and a target nucleic acid.

Another aspect of the invention provides methods of detecting target nucleic acids comprising amplifying target nucleic acids, and blocking amplification of other nucleic acids, the detection of which is not desired. Such methods generally comprise providing a sample that may comprise nucleic acid from at least one selected strain of an organism and nucleic acid from at least one non-selected strain of the organism. Also provided are multiple primers substantially complementary to portions of nucleic acids from both selected strains and non-selected strains of the organism. The sample is exposed to at least one nucleic acid analog probe that is sufficiently complementary to a portion of the nucleic acid from at least one non-selected strain to block its full length amplification between the plurality of primers. The nucleic acid from at least one selected strain is amplified between the multiple primers and detection of such amplification product indicates the presence of at least one selected strain in the sample.

In a preferred embodiment, methods of the invention are used to bias a screening assay toward the diagnostically most-relevant strains or species of a disease organism. Accordingly, methods of the invention comprise exposing a biological sample to primer pairs for amplification of nucleic acids from selected strains or variants of a disease organism, and blocking amplification of nucleic acids from non-selected strains or variants of the organism. Preferably, the primer pairs used in methods of the invention universally amplify nucleic acid of all strains of the disease organism. Amplification is blocked only in non-selected strains or variants of the organism, such that only nucleic acids from selected strains or variants are amplified.

In a highly preferred embodiment, methods of the invention are used to selectively amplify high-risk strains of an infectious organism. In such methods, consensus primers for amplification of a preselected region of the infectious organism's genome are used. Alone, these primers are capable of amplifying nucleic acid from most or all of the strains or variants of the disease organism. However, in methods of the invention, amplification of non-selected strains or variants is blocked such that any amplicon produced is representative of only the unblocked strains or variants.

For example, methods of the invention are used to selectively detect high-risk strains of HPV. An amplification reaction is conducted in the presence of HPV consensus primers and one or more peptide nucleic acid (PNA) blocking probes that hybridize only to a region at or between the primers in non-selected low-risk strains of HPV. The PNA blocking probes prevent amplification of nucleic acids from low-risk strains (i.e., full-length amplification between primers is prevented), while nucleic acids from high-risk strains to which the PNA blocking probes do not hybridize are amplified.

Methods of the invention are useful with any nucleic acid amplification method, such as polymerase chain reaction (PCR), ligase chain reaction (LCR), the rolling circle replication system, branched chain amplification, nucleic acid based sequence amplification (NASBA), Cleavase Fragment Length Polymorphism (see, e.g. U.S. Pat. No. 5,719,028, incorporated herein by reference), and Isothermal and Chimeric Primer-initiated Amplification of Nucleic Acid (ICAN), and Ramification-extension Amplification Method (RAM) (see, e.g. U.S. Pat. No. 5,719,028, 5,942,391, incorporated herein by reference). Methods of the invention are useful to detect the presence in a biological sample of any disease organisms, including viruses and bacteria, such as herpes, hepatitis, gonorrhea, streptobacillus, HPV, HIV, and others.

These and other advantages and aspects of the invention will be understood upon consideration of the following detailed description thereof.

BRIEF DESCRIPTION OF THE DRAWINGS

The drawings are not necessarily to scale, emphasis instead generally placed upon illustrating the principles of the invention.

FIG. 3 is an ethidium bromide-stained gel showing selective amplification using PNA probes in accordance with methods of invention illustrated by FIG. 1;

DETAILED DESCRIPTION OF THE INVENTION

Figure 1:
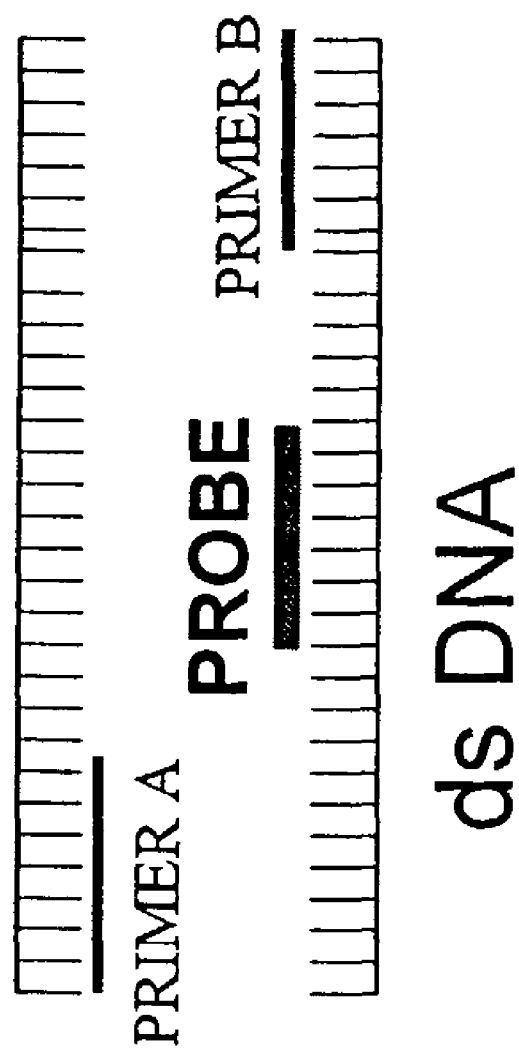
FIG. 1 provides a schematic illustration of certain methods of the invention.

In one aspect, methods of the present invention comprise screening patient samples for the presence of a high-risk HPV variant using at least one PNA probe. In a preferred embodiment, PNA probes that hybridize to portions of nucleic acids of multiple HPV types are used. Accordingly, the invention allows simultaneous detection of multiple strains or types of HPV.

Several PNA probes have been shown to cross-hybridize with nucleic acids from multiple HPV strains. Thus, in some instances, a single probe or a mixture of probes may be used to screen for the presence of multiple strains in a single sample. Also according to the invention, a PNA probe which hybridizes only to nucleic acid of a single HPV strain may be used to specifically identify and/or type that strain in a sample. Such highly specific probes can be used in series or in parallel by, for example, utilizing differentiable markers attached to the probes. A mixture of such highly specific probes or a mixture of such highly specific probes and cross-hybridizing probes may be used to identify multiple strains of HPV, preferably all the high-risk ones and only the high-risk ones.

Hybridization screening as described above also may be performed in a preservative solution, such as PreservCyt®, thereby combining cytological screening of a patient sample (e.g., a PAP smear) with HPV screening. The PreservCyt solution is described in co-owned U.S. Pat. No. 5,256,571, incorporated herein by reference.

According to methods of the invention, PNA probes are designed to be substantially complementary to portions of nucleic acids of one or more HPV types. HPV DNA sequences can be found in numerous public databases, such as GENBANK. PNA probes for use in the invention were designed to hybridize to homologous regions of one or more HPV strains. In a preferred embodiment, homologies that are common among high-risk HPV strains but not common among low-risk HPV strains are selected to ensure the specificity of PNA probes to high-risk types of HPV DNA only.

A preferred region of homology is the HPV L1 consensus region. The L1 region encodes for the major capsid protein of HPV and is retained whenever viral integration occurs in a cell. Other regions in the viral genome; e.g., the E6 open reading frame, described in U.S. Pat. No. 5,888,724 to Silverstein et al. and incorporated herein by reference, can also be used to generate homologies.

DNA sequences of the L1 regions of various HPV types were downloaded from GENBANK. L1 regions of high-risk HPV types were then compared using Vector NTI software (Informax Inc., North Bethesda, Md.) to establish areas of homology. Thereafter, areas of homology that are common among known high-risk types of HPV but not common among low-risk types of HPV were selected. This was to ensure that any PNA probe so constructed would exhibit maximal specificity for the high-risk types of HPV but minimal or no specificity for the low-risk types of HPV. The selected sequences were then analyzed with the Vector NTI program to discard any sequence that would form significant secondary structure (e.g., hairpins).

The regions of homology were then used to generate PNA probes useful in screening assays. Examples of the probes generated are shown in SEQ ID NOS.: 1-5. Typically, the probes should be short enough to stay in solution, i.e., less than 18 or 19 bases. In constructing the probes, preferably for any stretch of 10 bases in a sequence, there is no more than 6 purines. Also, 4 to 5 purines in a row, especially 3 guanines in a row, preferably should be avoided. A preferred length of a PNA probe is 8 or more units. The present invention also contemplates the use of hybrids between PNA and other nucleic acids, such as DNA and RNA, as probes for detecting multiple strains of interest. PNA-DNA chimeras as described in Uhlmann's "Peptide Nuclic Acids (PNA) and PNA-DNA Chimeras: From High Binding Affinity Towards Biological Function," *Biol. Chem.* 1998, 379 (8-9): 1045-52, the disclosure of which is incorporated herein by reference, can be useful in methods of the present invention.

Once the sequence of a PNA probe is finalized, a probe can be synthesized, purified and labeled according to methods known to those skilled in the art. For example, such methods are disclosed in PCT publication WO92/20702, U.S. Pat. Nos. 5,539,082 to Neilsen et al. and 5,731,416 to Garner, all incorporated herein by references. Such synthesis, labeling (e.g., with biotin) and purification of PNA probes can also be obtained from commercial vendors such as PerSeptive Biosystems Inc. (Framingham, Mass.).

"Molecular beacon" probes may also be employed in the methods of the present invention for direct visualization of hybridization between a probe and a target template. Molecular beacon probes are described in Tyagi et al., PCT application No. WO 95/13399 and Tyagi et al., PCT application No. WO 97/39008, which are both incorporated herein by reference. Molecular beacons are single-stranded nucleic acid probes that possess a stem-and-loop structure in which the loop portion of the molecule is a probe sequence complementary to the target nucleic acid sequence. The stem is generated by the annealing of two complementary arm sequences, each located at either end of the probe sequence. The arm sequences are unrelated (i.e., not complementary) to the target sequence and each arm is labeled at its end. To one arm is attached a fluorescence moiety (i.e., at the 5' terminal phosphate) and to the other a non-fluorescent quenching molecule (i.e., at the 3' terminal hydroxyl group). In its nascent state, the molecular beacon emits no fluorescence. This is because the fluorescent-quencher pair is selected such that energy gained by the fluorophore is transferred to the quencher and is dissipated as heat, an occurrence that is referred to as fluorescence resonance energy transfer (FRET). At temperatures slightly above $T_m$, the stem portion of a molecular beacon unfolds and exposes the probe section of the molecule to target strands. Once exposed, the beacon and target hybridize.

Upon hybridization, a molecular beacon interacts with the target and undergoes a conformational change whereby the arm sequences of the beacon are forced apart such that the fluorophore and the quencher are physically distant from each other and their original positions. When the fluorophore is no longer in the proximity of the quenching molecule, FRET is no longer possible, and the fluorophore will then emit detectable light of appropriate wavelength when excited. When the PNA probe in accordance with the invention is constructed as a molecular beacon molecule, having a loop portion of PNA complementary to target nucleic acids, the hybridization between the probe and the target template can be detected using a fluorescence reader, either in "real-time" or "endpoint" fashion.

The PNA probes of the present invention are contemplated to be useful in any detection assay of HPV genetic materials. In one embodiment, sample DNA isolated from a cervical specimen previously suspended in PreservCyt solution is first and optionally amplified using PCR with a pair of consensus primers, MY09 and MY11. These primers bind to different segments of HPV DNA's L1 region and amplify both DNA of high and low risks HPV strains. Amplification product is then contacted with biotin-labeled PNA probes specific for the DNA of high-risk HPV strains and allowed to hybridize. The solution containing hybridized PNA:DNA duplex is then applied to avidin-coated microtiter plates. After appropriate incubation and wash, a labeled antibody able to distinguish a PNA:DNA duplex from other nucleic acid complex is used for visualization of any hybridization. Such antibody is known in the art and described, e.g., in Hansen et al.: "Detection of PNA/DNA Hybrid Molecules by Antibody Fab Fragments Isolated from a Phage Display Library," *J Immunol Methods*, 1997 203(2): 199-207, incorporated herein by reference. The antibody may be labeled with a detectable marker including but not limited to: a radioisotope, or a calorimetric marker (e.g. digoxigenin), a luminescent marker, a fluorescent marker or an enzyme (e.g. alkaline phosphatase). Such markers are known in the art. Further, the primary antibody can in turn be recognized by a labeled secondary antibody for detection purpose.

In another embodiment of the invention, biotin-labeled DNA probes such as ALU probes are first used to hybrid-capture HPV DNA of all types onto an avidin-coated microtiter plate. After appropriate incubation and wash, PNA probes are added to the plate for hybridization. Detection of hybridization can be carried out using antibodies as described in the previous paragraph.

The present invention also includes kits that contain probes made in accordance with the invention or preservation solution or both, and may include other reagents needed for a detection assay. For example, a kit may include materials, instruments and devices for taking cervical samples, for storing the samples and for isolating and purifying genetic materials from the samples. An in vitro hybridization kit may include multiple probes, e.g., PNA probes made in accordance with the invention and ALU oligonucleotide probes, and other reagents needed for hybridization reactions. Any of these probes may be labeled, e.g., with biotin or a fluorophore. Kits made in accordance with the present invention may further include enzymes, primers (e.g., MY09/MY11), buffers and other reagents for a nucleotide-amplification reaction. An in situ hybridization kit may include enzymes, fixation solution, buffers and other reagents needed for slide preparation, signal amplification and other techniques employed in in situ hybridization. A kit may also include enzymes, antibodies, substrates and other reagents needed for labeling, detection and visualization of a target molecule. Such kits may also include probes and reagents needed for further HPV typing.

In another aspect of the invention, methods and materials are provided for clinical assay of a biological sample to identify one or more selected nucleic acid variants by blocking amplification of non-selected variants. In a preferred embodiment, methods are used to detect one or more selected strains or variants of a disease organism, such as the DNA or RNA of a bacterium, yeast, other microbe, or a virus. The methods comprise amplifying a disease organism's nucleic acid using consensus primers capable of amplifying nucleic acids from several and preferably all strains or variants of the organism, while blocking amplification of nucleic acids from non-selected strain(s). The presence of amplification product indicates presence of the selected strain(s). No labeled probes are necessary. No probes that hybridize with sequences characteristic of the strain(s) of interest are necessary either. In a preferred embodiment, PCR is used to amplify the nucleic acid, and blocking-probes made of PNA are used.

In a preferred embodiment, a gynecological cell sample is obtained from a female subject to screen for strains of HPV that indicate high-risk of cervical cancer. Such a sample may be suspended, for example, in a PreservCyt® preservative solution. DNA from the sample is isolated and purified using kits and methods well known to one skilled in the art.

A pair of consensus primers, MY09 and MY11, are then selected as primers for a PCR reaction as illustrated in FIG. 1. Primers MY09 and MY11 (SEQ. IDS. NOS. 10 and 11) bind to portions of the HPV L1 consensus region. The L1 consensus region is preferred because it is retained whenever viral integration occurs in a cell. However, other regions in the HPV viral genome, such as the L2, E1, E6 and E7 open reading frames, are also useful as candidate region for amplification. HPV-specific PNA blocking probes are constructed based upon published HPV DNA sequences (e.g., from GENBANK). In accordance with the present invention, a blocking probe comprising PNA is designed to be substantially complementary to a portion in the L1 region, between the hybridization sites for primers MY09 and MY11, only of low-risk HPV strains. A subsequent PCR selectively amplifies only DNA from high-risk strains because exponential amplification of low-risk strains is blocked by the PNA probe. Segments between the hybridization sites of the primers up to the blocked region in the low-risk strains are replicated in a linear fashion rather than in an exponential way, resulting in no detectable amount of amplicon. In a preferred embodiment, the probe hybridizes to a region adjacent to a primer hybridization site, eliminating even truncated amplification product. Consequently, in methods of the invention, amplification product, i.e., a mass of nucleic acid above baseline level, is detectable through conventional DNA detection methods such as ethidium bromide staining, CYBR Green staining and other DNA staining. The presence of amplicon indicates the presence of high-risk strains in the sample. The size of the amplicon may be determined through simple gel electrophoresis or other methods and is used to further substantiate the presence of a high-risk strain. Conversely, the absence of amplification product indicates the lack of high-risk strains in the sample.

Multiple blocking probes can be constructed with specificity for nucleic acids from a different subset of the non-selected strains. When these multiple blocking probes are used as a "cocktail" in an amplification reaction, they together block amplification of all the non-selected strains. Therefore, in a particularly preferred embodiment, probes are constructed to block as many low-risk HPV strains as possible, such as type 11, 16, and 42-44, without blocking amplification of any high-risk strains. In a further preferred embodiment, at least one probe blocks amplification of all low-risk HPV strains through hybridization with low-risk HPV DNA within the region intended for amplification. Subsequent detection of amplification product, which is full-length between the primer set, indicates presence of high-risk strains in the sample while absence of amplification product indicates the lack of high-risk strains.

Figure 2:
FIG. 2 provides a schematic illustration of more methods of the invention.

Referring to FIG. 2, a nucleic acid analog probe is constructed to hybridize partially or completely with a hybridization site of at least one of the primer pair. In a preferred embodiment, probes are made of PNA molecules or chimeras between PNA and another nucleotide such as DNA. Other types of probes that block amplification through sequence-specific hybridization may also be used. And the blocking probe, whether used in accordance with FIG. 1 or 2, can be constructed to be a molecular beacon as described earlier. A molecular beacon blocking probe allows real-time detection of hybridization between the blocking probe and non-select strain's template.

Compared to DNA or RNA, PNA has a higher affinity for a substantially complementary nucleic acid template. Therefore, in a situation where a PNA probe competes with a DNA or RNA primer for part or all of a hybridization site, hybridization between the PNA probe and the nucleic acid template is favored. As a result, full-length amplification between the hybridization sites of the primer set will be inhibited. See U.S. Pat. No. 5,891,625 to Buchardt et al., the entirety disclosure of which is incorporated herein by reference.

Blocking probes used in embodiments illustrated by FIG. 2 may include one or multiple ("cocktail") blocking probes. Similar to what is described of the embodiments related to FIG. 1, detection of amplification product will indicate the presence of selected strains such as the high-risk strains of HPV.

Exemplary Method for Detecting HPV in a Cervical Scraping

A. Hybridization Assay using PNA Probes

Methods of the invention are used to screen for the presence of HPV in cervical scrapings from several female patients. Scrapings are obtained by swabbing and placed in PreservCyt® solution at a concentration of about $2.0 \times 10^5$ cells per ml. The solution containing cells is mixed by vortex, and an aliquot of the sample is taken to make a "ThinPrep" slide for cytological analysis, as described in U.S. Pat. No. 5,143,627 to Lapidus et al., incorporated herein by reference. Specifically, the slide, where sample cells are uniformly transferred, is prepared using a ThinPrep Processor 2000® (Cytyc Corporation, Boston Mass.).

A second aliquot of the sample solution is obtained for HPV analysis. The Buccal Swab DNA kit of Epicentre Technologies, Inc. (Madison, Wis.) is used for DNA extraction. The MY09/MY11 consensus primers (Research Genetics, Inc., Huntsville, Ala.) are used for PCR amplification.

For PCR, 100 ng (or 5 μl) of target DNA is mixed to a total volume of 50 μl with 10 mM Tris-HCl (pH 8.3), 5-mM KCl, 6 mM $MgCl_2$, 22 μM dNTP, 50 pmole of primer, 5 pmole β-globin primers PC04 and GH20, and 2.5 units Amplitaq DNA polymerase (Perkin Elmer Getus, P. W. Roche Molecular Systems, Inc., Branchburg, N.J.). Amplification of the β-globin gene is performed as a control to determine whether the sample is appropriate for HPV detection by PCR. PCR parameters are set at 35 cycles (95° C.-60 sec/55° C.-60 sec/72° C.-60 sec). Amplification products are detected by electrophoresis of one fifth volume of the reaction mix on a 1% agarose gel stained with ethidium bromide. Sample DNA is then extracted from the gel and in situ hybridization assay (as described below) is used to evaluate HPV status.

EXAMPLES

Example 1

Constructing and Testing of PNA Probes

Biotin-labeled PNA probes complimentary to several high-risk types of HPV DNA were generated. The PNA probe sequences were based on areas of homology found in the L1 consensus region amplified by the MY09/MY11 degenerate primer set with information from the GENBANK database. Five PNA sequences are identified as SEQ. ID NOS. 1-5 below. Biotin-labeled PNA, 14 to 15 bases in length were synthesized to specification by PerSeptive BioSystems (Framingham, Mass.).

HPV infected gynecological samples were stored in methanol-based PreservCyt solution (Cytyc Corporation, Boxborough, Mass.). DNA from these samples was isolated and purified using Epicenter's Buccal swab DNA extraction kit (Madison, Wis.) with the following steps: 2 ml of the PreservCyt suspension was pelleted by centrifugation at 8,000×g for 5 minutes. The supernatant was removed and the pellet resuspended in Epicenter's DNA extraction fluid and incubated at 60° C. for 30 minutes, 98° C. for 10 minutes, and chilled on ice for 5 minutes. The resulting supernatant containing the extracted DNA was recovered by centrifugation at 8,000×g for 5 minutes.

The HPV DNA genotypes of residual PreservCyt cell suspensions were first determined by two separate methods. The first typing method was Polymerase Chain Reaction-Restriction Fragment Length Polymorphism (PCR-RFLP) analysis of HPV consensus primers (MY09/MY11)-amplified L1 consensus region of HPV. PCR-RFLP was performed on specimen according to methods described by Lungo et al. in "Typing of HPV by PCR Amplification with L1 Consensus Primers and RFLP Analysis," Mol. & Cell Probes, v.10, p 145-52, 1992, incorporated herein by reference. Specifically, purified DNA was amplified in the presence of P-32 labeled CTP (and other appropriate NTPs) and then the amplicon was digested concurrently with Pst I, Rsa I, and Hae III. The restriction digest product was analyzed on polyacrylamide gels and HPV type size assigned based on HPV DNA standards. Detection was achieved by exposure to X-ray films. In addition to PCR-RFLP, each positive specimen was typed by a second method using a commercially available hybridization HPV DNA typing kit (Alphagenics Diaco Biotech, Trieste, Italy) according to manufacture's instructions. Purified sample DNA was first amplified with DIG-labeled MY09/MY11 primer. The amplicon was subsequently hybridized with biotin-labeled DNA probes specific to each type of HPV DNA. Hybridized duplexes were captured on avidin-coated microtiter plates and detected with enzyme-bound antibodies recognizing the DIG-labeled nucleic acid.

After a specific aliquot of sample DNA has been independently typed by these two methods, the DNA was amplified using MY09/MY11 primers to later be hybridized with constructed PNA probes. PCR-amplified DNA samples of various types of HPV were loaded on different columns of a 0.8% agarose gel and underwent PAGE. The size and presence of HPV L1 consensus amplicon were determined by Ethidium Bromide staining of PAGE samples. The amplicons in the gel were depurinated, washed, and then denatured at room temperature. The gel was then neutralized (0.5 M Tris-HCl/1.5 M NaCl) at room temperature and the DNA transferred overnight from the agarose gel to a nylon membrane (Biodyne B membrane, PALL) through capillary diffusion. Successful transfer was determined by the absence of ethidium bromide bands on processed gel. The DNA was thereafter fixed to the membrane by heating for 30 minutes at 80° C. The membrane was re-hydrated in 2×SSC and pre-hybridized with blocking solution (100 mg/ml of salmon sperm DNA/5×SSC/5× Denhardt's solution/0.1% SDS) for 30 minutes at 68° C. Subsequently the membrane was hybridized with 20 nM of denatured biotin-labeled PNA probe overnight at 65° C.

After the membrane was removed from the hybridization solution and washed, presence of biotinylated PNA: DNA hybrids was established by chemiluminescent substrate assay which relies on phosphatase enzyme as the catalyst (Phototope Star detection kit from New England BioLabs). Final detection was obtained by exposure of the Southern blot to X-ray film (Kodak).

Table 1 shows the testing result for some of the PNA probes. A plus sign indicates that significant hybridization was observed between the PNA probe constructed according to a particular Sequence ID (row) and the particular type of HPV (column). A minus sign indicates the absence of such observation. A blank cell in the table indicates that hybridization reaction has not been carried out as specified yet.

TABLE 1

| Seq. Id. | Type 6 | Type 11 | Type 16 | Type 18 | Type 31 | Type 33 | Type 35 | Type 39 | Type 45 | Type 51 | Type 52 | Type 53 | Type 56 | Type 58 | Type 68 |
|---|---|---|---|---|---|---|---|---|---|---|---|---|---|---|---|
| 1 | — | — | + | — | — | — | — | — | — | — | — | — | — | — | — |
| 2 | — | — | + | + | — | — | + | + | — | — | — | — | — | — | — |
| 3 | + | + | — | + | — | + | — | — | — | + | — | — | + | — | — |
| 4 | — | — | — | — | — | + | — | — | — | — | — | — | — | — | — |
| 5 | — | — | — | — | — | — | — | + | + | — | — | — | — | — | + |

Detection of a target nucleic acid of HPV through hybridization with a labeled PNA probe prior to gel electrophoresis was also tested. PCR-Amplified DNA (1 ul) was mixed with biotinylated PNA probe I (SEQ. ID NO. 1) (20 pM) in varying dilutions of the hybridization buffer. Amplicons, in the presence of PNA probes, were denatured for 10 minutes at 95° C., annealed rapidly and PNA:DNA duplexes were isolated on a 3% agarose gel. The presence of DNA may be determined by ethidium bromide staining. Thereafter, the DNA, without being denatured, was transferred onto a nylon membrane through capillary diffusion. Fixation to nylon was performed as described previously. DNA:PNA duplexes were detected and visualized using chemilumenscent substrate and X-ray films as described previously. In dilutions of hybridization buffer ranging from 1:1 to 1:1000, significant hybridization was observed between probe I and HPV DNA Type 16 from Caski cells, but none between the same probe and HPV DNA Type 18 from Hela cells. The pre-gel hybridization eliminates the need for in-gel denaturation and tedious hybridization and stringency washings, reduces hands-on time for detection assay, requires relatively small amount of PNA probes and works well on PCR products.

Example 2

In situ Hybridization

Step 1: Slide Preparation:

Cells fixed on ThinPrep slides are digested with proteolytic enzyme (i.e., 500 ul of 10 ug/ml proteinase K in 2×SSC, or with 500 ul of 0.2 N hydrochloric acid solution containing 0.05%-0.15% pepsin) at 37° C. for 30 minutes. The slides are then washed in 2×SSC for 2 minutes, ethanol dehydrated and air dried. Fifteen to 20 ul of the hybridization mixture containing 1 to 20 nM PNA probes are applied to each slide. Slides are then covered with glass coverslip and sealed.

Step 2: Hybridization

The PNA probes and target DNAs are co-denatured by placing the slides inside a thermocycler (MJ Research, Inc. Watertown, Mass.) and quickly bringing and maintaining the temperature of the thermocycler at 80° C. for three minutes. The interior temperature is afterwards rapidly dropped to 37° C., and the incubation is allowed to proceed from 15 minutes to 2 hours. Next, the slides are removed from the thermocycler, the coverslip are removed with forceps, and slides are washed for five minutes in 2×SSC at 75° C. Slides are then transferred to a Coplin jar containing 40 ml of phosphate buffered saline containing 0.05% Tween20 for 2 minutes.

Step 3: Post-Hybridization Wash and TSA Amplification

Amplification in the in situ assay can be performed by using commercial TSA-Indirect kit of NEN (Life Science Product at Boston, Mass.). Tyramide Signal Amplification systems are described by Sano et al. in "In situ hybridization with biotinylated tryamide amplification: Detection of human papillomavirus DNA in cervical neoplasia," *Modern Pathol* 1998; 11:19-23, incorporated herein by reference. Basic steps can be performed as follows: each slide from the previous step is incubated with 100 ul TNB Blocking Buffer (0.1 M Tris-HCl, pH 7.5, containing 0.15 M NaCl, and 0.5% blocking reagent) in a humid chamber for 30 minutes at room temperature. Plastic coverslips are used on the slides to reduce evaporation. Each slide receives 100 ul of strepavidin-horseradish peroxidase reagent (1:100 dilution in TNB Blocking Buffer), and is thereafter incubated for 30 minutes at room temperature while covered by cover slips. Next, slides are washed at room temperature with agitation in TNT Buffer (0.1 M Tris-HCl, pH 7.5 containing 0.15 M NaCl and 0.05% Tween), and to each slide 300 ul of biotinyl-tyramide is added. After incubation at room temperature for 3 to 10 minutes, the slides are once more washed in TNT buffer.

Step 4: Chromogenic Detection

About 100 ul of strepavidin-alkaline phosphatase (1:100 dilution in TNB Buffer) is added to each slide. Slides are incubated in a humid chamber while covered at room temperature for 5 to 10 minutes, and each slide is then washed in TNT Buffer. Hybridized PNA probes are detected by BCIP-NBT detection system according to manufacturer's instruction.

Step 5: Counterstain and Mounting

Slides are washed in distilled water, then counterstained with Eosin, coverslipped and mounted.

B. Use of PNA in Selective Amplification of HPV DNA

A "ThinPrep" slide and sample DNA were prepared from suspended cervical scrapings specimens as described in Part A.

DNA sequences of the L1 consensus region of HPV strains available from GENBANK are used to generate PNA probes useful in the selective blocking of amplifications of the DNA templates extracted from the second aliquot. The PNA probes used are shown in SEQ ID NOS.: 6-8. Typically, the probes should be short enough to stay in solution, i.e., less than 19 bases. In constructing the probes, for any stretch of 10 bases in a sequence, there are ideally fewer than about 7 purines.

PCR amplification reactions are then performed in the presence or absence of the probes with the MY-09/MY-11 primer set (SEQ. ID. NOS. 10 and 11) or modification thereof under the following conditions: initial denaturation step at 95° C. for 5 minutes, then 35 cycles of 95° C.—30 sec/54° C.—30 sec/72° C.—60 sec, with a final extension step of 2 minutes at 72° C. Other thermal cycling conditions may be also used for this application (e.g., initial denaturation step at 95° C. for 5 minutes, followed by 35 cycles 95° C.—30 sec/4° C.—60 sec/55° C.—30 sec/72-60 sec, with a final extension of 72° C. for 2 minutes. Additional alternatives may include a 25° C. PNA annealing temperature in place of the 4° C. step, as well as shortening the 4° C. step from 60 sec to 30 sec). The use of MY09 and MY11 primers to amplify and sequence the HPV L1 region is described in more detail in Bauer et al.'s "Genital Human Papillomavirus Infection In Female University Students As Determined By A PCR-Based Method," *JAMA* 1991; 265:472-477, incorporated herein by reference.

PCR master mix may be in a final volume of 20 ul and consisted of 10 mM Tris-HCl pH 8.3, 25 mM KCl, 5 mM $MgCl_2$, 200 µM of dNTP, 100 nmoles of each HPV L1 consensus primer, 1.0 units of Platinum Taq DNA polymerase (Gibco) and 100-750 ng of purified cellular DNA. DNA concentrations are determined by UV spectrophotometry by calculating the ratio between the readings at 260 nm and 280 nm. An $OD_{260}/OD_{280}$ provides an estimate of the purity of nucleic acids. The final PNA concentration is usually set at 10 µM. Amplification products can be detected by electrophoresis of three-fourths of the reaction mix on a 2% agarose gel stained with ethidium bromide.

EXAMPLES

Example 3

Testing PNA Probes Constructed According to Embodiments Illustrated by FIG. 1

Two PNA probes, VI and VII (SEQ. ID. NOS. 6-7), were constructed in accordance with embodiments illustrated by FIG. 1. The sequences of both PNA probes VI and VII are substantially complementary to a homologous portion of low-risk HPV strains 6 and 11. Both probes bind to a portion between the binding sites for primer sets MY09/MY11.

DNA solutions of a known HPV strain were used to test the selective blocking capabilities of both probes in accordance with the present invention. As shown in FIG. 3, no PCR amplicon was observed in DNA samples of HPV strain 11 when either HPV probe VI and VII was used. PCR amplicon of the expected length was detected through ethidium bromide staining of the DNA of HPV strains 16 or 18 in the presence of either probe VI and VII. These results indicated that probes VI and VII, as they were designed for, were able to block amplification of HPV strain 11 and not 16 or 18.

Example 4

Testing PNA Probes Constructed According to Embodiments Illustrated by FIG. 2

A modified consensus primer MC01, (SEQ. ID. NO. 9) was constructed to be used in conjunction with MY09 and was capable of amplifying multiple HPV strains including strain 18. PNA probe VIII (SEQ. ID. NO. 8) was designed to comprise part of the primer MC01 with two base-pair modifications, which makes the probe 100% complementary to HPV strain 18's DNA and not to any other strains. PNA probe VIII was expected to compete with the modified consensus primer MC01 for binding to the DNA of HPV strain 18.

Figure 4:
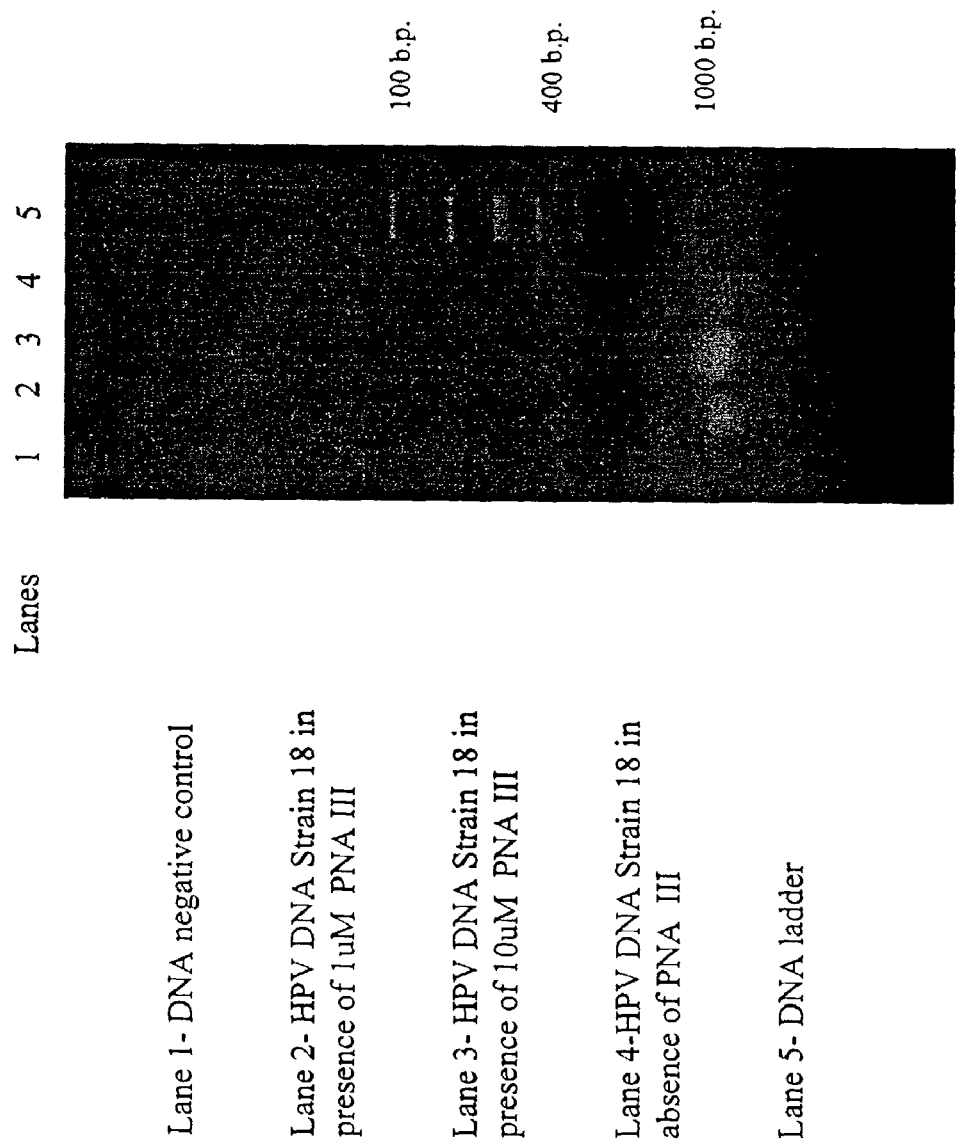
FIG. 4 is another ethidium bromide-stained gel showing DNA amplification blocked by a PNA probe in accordance with methods of invention illustrated by FIG. 2.

As shown in FIG. 4, DNA solutions of HPV strain 18 was used to test HPV probe VIII. No PCR amplicon was observed when various concentrations of HPV probe VIII were used.

PCR amplicon of the expected length was detected through ethidium bromide staining of DNA sample in the absence of PNA probe VIII. These results indicated that probe III was able to compete and block amplification of HPV strain 18.

What is claimed is:

1. A method for detecting the presence of a target nucleic acid of a human papilloma virus (HPV) in a sample cell, comprising the steps of:

suspending a sample cell that may comprise a target nucleic acid of a HPV in a cell preservative solution separating a said target nucleic acid from said sample cell wherein said separated target nucleic acid remains in said cell preservative solution wherein said cell preservative solution comprises an alcohol in an amount sufficient to preserve said sample cells without coagulation;

contacting said target nucleic acid in said cell preservative solution with at least one probe comprising at least one peptide nucleic acid (PNA), said at least one probe being substantially complementary to portions of nucleic acids of multiple HPV types;

allowing said at least one probe to hybridize with said target nucleic acid, if present, in said cell preservative solution; and detecting hybridization between said at least one probe and said target nucleic acid in said solution;

wherein the detection of said hybridization is indicative of the presence of a target nucleic acid of a HPV in a sample cell.

2. The method of claim 1, wherein said sample cells come from a subject and wherein the presence of said target nucleic acid sequence indicates a risk of tumor growth in said subject.

3. The method of claim 2, wherein said tumor growth is associated with either cervical or endocervical carcinoma.

4. The method of claim 1, wherein the presence of said target nucleic acid sequence is indicative of the presence of a particular type of HPV.

5. The method of claim 4, wherein said particular type of HPV is selected from the group consisting of types 16, 18, 31, 33, 35, 39, 45, 51, 52, 56, 58, 59, 68 and 70.

6. The method of claim 1, wherein absence of said target nucleic acid sequence is diagnostic of absence of infection by HPV.

7. The method of claim 1, wherein absence of said target nucleic acid sequence is diagnostic of absence of infection by HPV types selected from the group consisting of types 16, 18, 31, 33, 35, 39, 45, 51, 52, 56, 58, 59, 68 and 70.

8. The method of claim 1, wherein absence of said target nucleic acid sequence is diagnostic of absence of infection by high-risk types of HPV.

9. The method of claim 1, further comprising amplification of said target nucleic acid.

10. The method of claim 9, wherein said amplification step comprises conducting a polymerase chain reaction.

11. The method of claim 1, further comprising capturing said target nucleic acid onto a solid support through PNA-DNA interaction.

12. The method of claim 1, wherein each of said at least one probe comprises at least 8 bases.

13. The method of claim 1, wherein said at least one probe comprises a nucleotide different from PNA.

14. The method of claim 1, wherein said at least one probe is selected from the group consisting of SEQ. ID. NOS. 1-5.

15. The method of claim 1, wherein said at least one probe is labeled with a detectable marker.

16. The method of claim 1 wherein said at least one probe comprises a molecular beacon probe.

17. The method of claim 1, further comprising using an antibody to recognize said hybridization.

18. The method of claim 1, wherein said cell preservative further comprises, an anti-clumping agent, and a buffer agent that maintains said solution at a pH within a range of about 4 to about 7.

* * * * *